United States Patent [19]
Bond et al.

[11] Patent Number: 5,618,992
[45] Date of Patent: Apr. 8, 1997

[54] DEVICE AND METHOD FOR MONITORING DEPOSITS IN A PIPE OR VESSEL

[75] Inventors: Derek Bond, Lagness; Raul A. Abreu, Horsham, both of England

[73] Assignee: The BOC Group plc, Windlesham Surrey, England

[21] Appl. No.: 537,197

[22] Filed: Sep. 29, 1995

[30] Foreign Application Priority Data

Oct. 3, 1994 [GB] United Kingdom ............ 9419886

[51] Int. Cl.$^6$ .................................................. G01F 23/26
[52] U.S. Cl. ........................................... 73/86; 324/671
[58] Field of Search .......................... 73/86, 304 C, 73/61.62; 324/663, 671, 686, 688, 689, 664; 361/277, 278, 279, 280

[56] References Cited

U.S. PATENT DOCUMENTS

| | | |
|---|---|---|
| 2,754,478 | 7/1956 | Goldsmith ............ 361/280 |
| 3,826,979 | 7/1974 | Steinmann ............ 324/688 |
| 4,568,874 | 2/1986 | Kramer ............ 73/304 C |
| 4,782,282 | 11/1988 | Bachman . |

FOREIGN PATENT DOCUMENTS

| | | |
|---|---|---|
| 0308004 | 3/1909 | European Pat. Off. . |
| 0061544 | 10/1982 | European Pat. Off. . |
| 0499841A1 | 8/1992 | European Pat. Off. . |
| 0517530A2 | 12/1992 | European Pat. Off. . |

*Primary Examiner*—Robert Raevis
*Attorney, Agent, or Firm*—David M. Rosenblum; Larry R. Cassett

[57] ABSTRACT

A non-intrusive device for attachment to a pipe or vessel through which a fluid flows for monitoring the accumulation of deposits on the interior surface of the pipe or vessel. The device comprises a tubular member having an internal cross-sectional configuration substantially matching that of the pipe or vessel. Additionally, the tubular member is made of an electrically insulating material and having associated therewith three spaced electrodes for monitoring the change of dielectric constant within the pipe or vessel.

6 Claims, 2 Drawing Sheets

DEVICE AND METHOD FOR MONITORING DEPOSITS IN A PIPE OR VESSEL

BACKGROUND OF THE INVENTION

The present invention relates to devices for attachment to a pipe or vessel through which a fluid flows for monitoring the accumulation of a substance of substances on the interior surface of the pipe or vessel.

In, for example, the semi-conductor industry a low pressure chemical vapor deposition process is used to apply a deposition to wafers or substrates in a vacuum furnace. In such a process, for example, dichlorosilane and ammonia pass through the vacuum furnace which has been loaded with wafers in order to deposit silicon nitride on the wafers, leaving ammonia, hydrogen chloride, excess dichlorosilane and hydrogen as waste gases. The waste gases exit via a fore-line, vacuum pump and exhaust line and ammonium chloride and other substances can be formed and deposited as a solid on the inside surface particularly of the exhaust pipe. This tendency for the ammonium chloride to leave an accumulative deposit on the inside surface of the exhaust pipe in particular has required the regular manual inspection of the exhaust pipe to ensure that the exhaust pipe doesn't become excessively blocked and thereby prevent the flow therethrough of the waste gas and/or put an unnecessary mechanical strain on the vacuum pump.

It has been known to place in the interior of the exhaust pipe a sensor for monitoring the build up of deposits such as ammonium chloride on the inside surface of the exhaust pipe. However, it has been found that by placing a sensor on the inside of the pipe only encourages deposits not only on the inside surface of the pipe but also on the sensor itself. Furthermore the actual presence of the sensor physically restricts the flow of waste gases through the exhaust pipe. It is an aim of the present invention to provide a non-intrusive device for attachment to a pipe or a vessel through which a fluid flows for monitoring the accumulation of deposits on the interior surface of the pipe or vessel.

SUMMARY OF THE INVENTION

According to the present invention, there is provided a non-intrusive device for attachment to a pipe or vessel through which a fluid flows for monitoring the accumulation of deposits on the interior surface of the pipe or vessel, comprising a tubular member having an internal cross-sectional configuration substantially matching that of the pipe or vessel, the tubular member being made from electrically insulating material and having associated therewith three spaced electrodes for monitoring the change of dielectric constant within the pipe or vessel.

Preferably each electrode is in the form of a circular ring extending circumferentially around the outside surface of the tubular member. Clearly each electrode will be electrically conductive.

The central electrode preferably is of greater width (axially) than the other electrodes in preferred embodiments, an active guard is present to shield the electrodes from earth, for example in the form of an elongate metallic cylinder.

BRIEF DESCRIPTION OF THE DRAWINGS better understanding of the invention, reference will now be made, by way of exemplification only, to the accompanying drawings in which.

DETAILED DESCRIPTION

Figure 1:
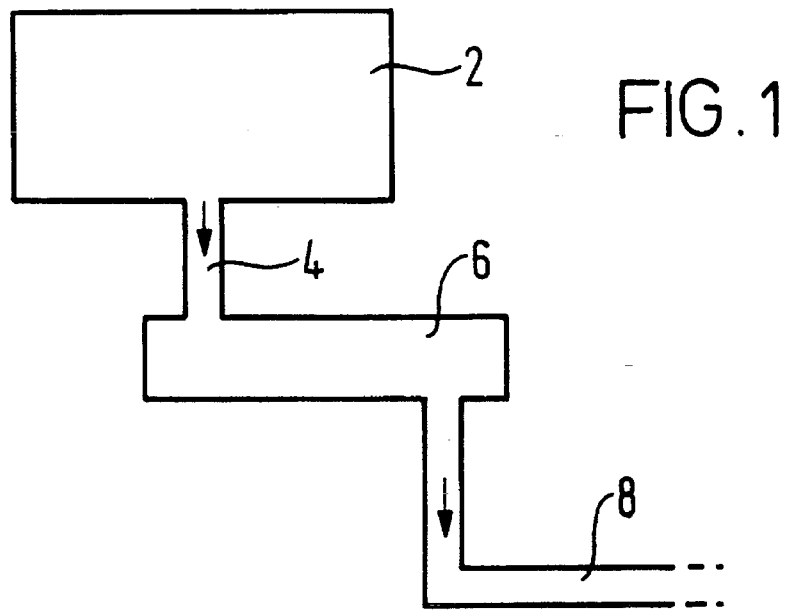
FIG. 1 is a schematic block diagram of a vacuum furnace and ancillary equipment for performing a low pressure chemical vapor deposition process.

Referring to FIG. 1, there is shown in a low pressure chemical vapor deposition process, a vacuum furnace 2 loaded with a plurality of wafers. A mixture of gases, for example, dichlorosilane and ammonia pass through the vacuum furnace 2 for depositing silicon nitride on the wafers and hydrogen chloride, ammonia, hydrogen and dichlorosiline leave the vacuum furnace 2 as waste gases passing through a fore-line 4, vacuum pump 6 and exhaust line 8.

As previously explained, it has been found that the ammonium chloride can deposit particularly on the inside surface of the exhaust line 8 and regular manual inspection of the exhaust line 8 is currently necessary to monitor the amount of deposition of ammonium chloride, as it accumulates on the inside surface of the exhaust line 8 in order to avoid complete blockage of the exhaust line 8 and/or overloading of the vacuum pump 6.

Figure 2:
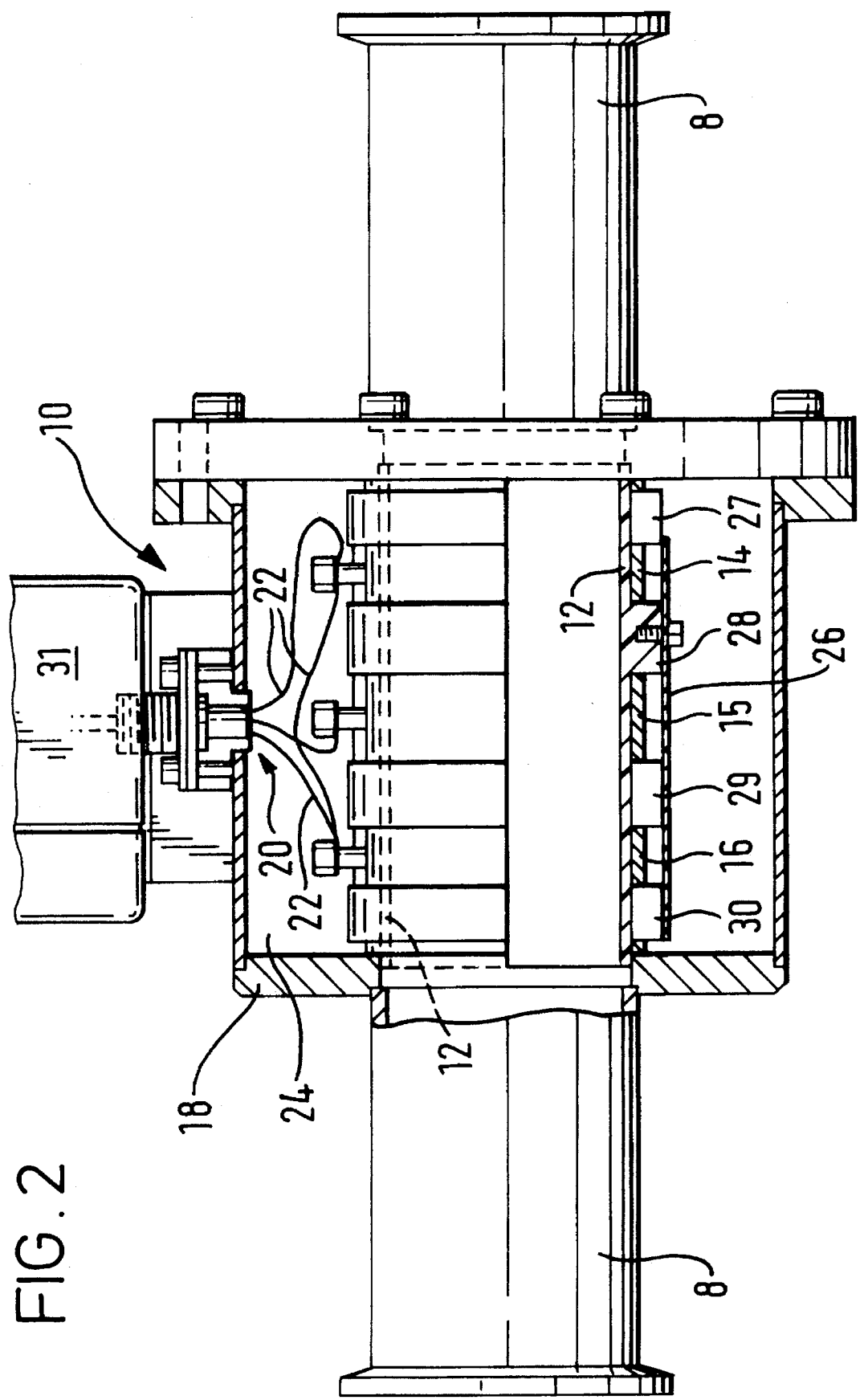
FIG. 2 is a side view (partly in cross-section) through a device of the invention for attachment to a pipe or vessel for monitoring the accumulation of a substance or substances on the interior surface of the pipe or vessel.

Referring more particularly to FIG. 2, a device 10 for attachment, for example, to or within the exhaust line 8 comprises a tubular member 12 made from electrically insulated material, for example PTFE, and having substantially the same internal cross-sectional configuration as that of the exhaust line 8. In this particular embodiment the exhaust line 8 and the interior of the tubular member 12 have a circular cross-sectional configuration. Mounted on the tubular member 12 are three electrodes 14, 15 and 16 spaced apart from each other and extending circumferentially around the outside surface of the member 12. Each electrode is made from an electrically conducting material, preferably stainless steel.

It can be seen that the central electrode 15 is wider (in the axial direction) than the other two (outer) electrodes 14 and 16 in accordance with preferred embodiments of the invention.

The electrodes 14, 15 and 16 are separated and electrically insulated by means of PTFE spacers 27, 28, 29 and 30, all being of circular shape and positioned around the member 12; spacer 28 is in fact an extension of the member 12.

An active guard 26 is present in the form of a cylindrical member made from an electrically conductive material, for example stainless steel, and surrounding the three electrodes 14, 15 and 16 by virtue of its being supported on the outer surfaces of the spacers 27, 28, 29 and 30.

Arranged around the tubular member 12 is a casing 18 made from an insulating material and having a port 20 through which extend electrical conductors 22 for connection to the electrodes 14, 15 and 16. As shown, the casing 18 defines an insulating air gap 24 surrounding at least a major portion of the length of the tubular member 12.

In use, the device 10 is releasably attached at a predetermined location in a vacuum exhaust pipe 8 by means known in the art such as clamps or flange-plates (not shown). Thereafter the electrodes monitor the change of dielectric constant within the pipe thereby giving an indication of the amount/state of deposit on the inside surface of the pipe 8. It will be apparent that the device 10 is non-intrusive in that there is no part of the device which extends into the inside of the exhaust pipe 8 and therefore the device offers no resistance to the flow of waste gases through the pipe 8.

The specific arrangement of the three electrodes in accordance with the invention has been found to provide a very sensitive means for monitoring the dielectric constant within the pipe by virtue of the type of electro-magnetic field present within the device 10.

The presence of the active guard 26 has been shown to improve the device in this respect by urging the electric field further towards the center of the tubular member 12.

In particular, the two outer electrodes 14, 16 act as earth/ground rings but have a relatively low electric potential applied thereto with substantially the same potential being applied to the guard 26. A higher electric potential is applied to the central electrode 15 and this in practice acts as the sensing element of the device.

The electric potential is applied and relevant measurements, in particular the change in dielectric constant, are made by means of a control box 31.

By continually monitoring the build up of deposits on the inside of the pipe 8 it will be possible to change the pipe before any unnecessary strain is placed upon the vacuum pump or the pipe itself becomes too blocked to be effective as a means of disposing of the waste gases from the vacuum furnace 2. Furthermore, it is hoped that any sudden or unexpected changes detected by the device 10 will give some early indication that a fault is likely to take place in the actual vacuum pump itself.

Figure 3:
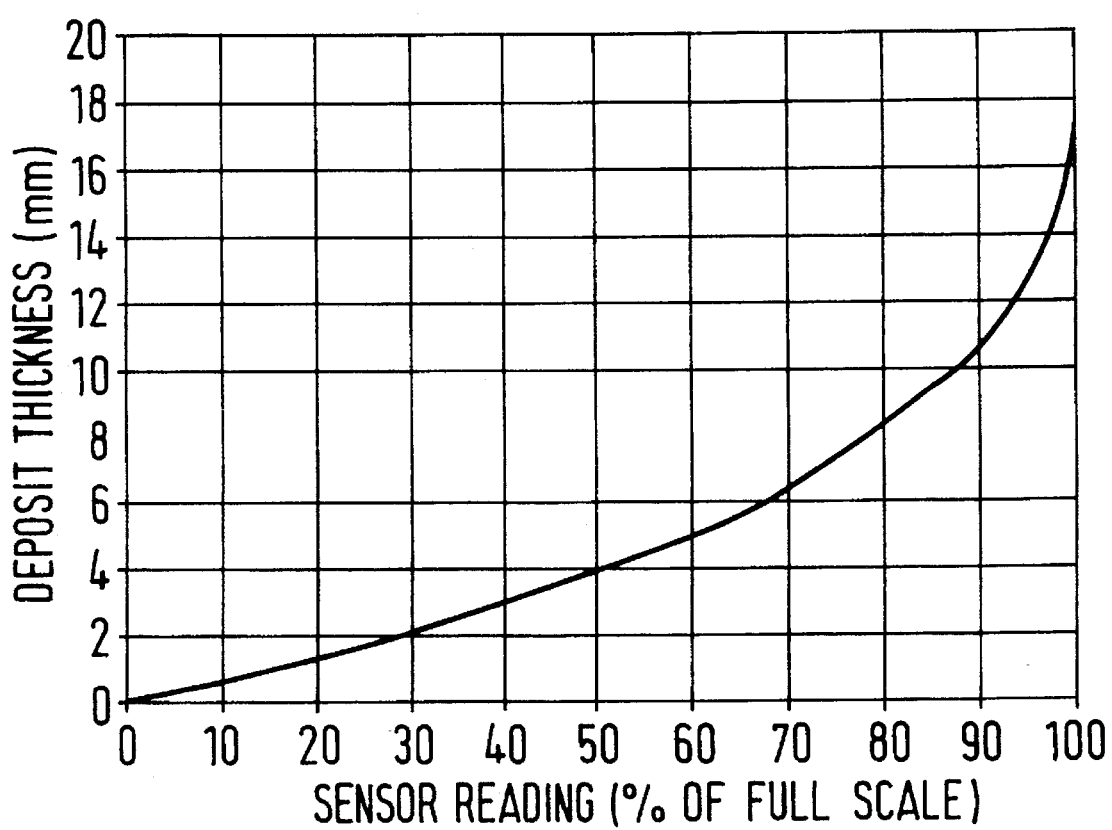
FIG. 3 is a graph illustrating the sensitivity of the device of the invention.

Turning to FIG. 3, the graph of a sensor reading in the device against the thickness of deposit inside the member 12 shows that it follows an exponential dependence curve.

Although the above embodiment has been described in connection with a low pressure chemical vapor deposition process it will be clear that the non-intrusive device disclosed will be equally as effective in other processes such as plasma enhanced chemical vapor deposition where waste fluids form deposits on the inside surfaces of pipes or vessels.

We claim:

1. A non-intrusive device for attachment to a pipe or vessel through which a fluid flows for monitoring the accumulation of deposits on the interior surface of the pipe or vessel, said device comprising a tubular member having an internal cross-sectional configuration substantially matching that of the pipe or vessel, the tubular member being made from an electrically insulating material and having associated therewith three spaced electrodes for monitoring the change of dielectric constant within the pipe or vessel, the three electrodes comprising two outlying electrodes and a central electrode located between the two outlying electrodes, each of said two outlying and central electrodes formed by a circular ring extending circumferentially around the outside surface of the tubular member and the central electrode having a greater width, as measured in an axial direction of said tubular member and said two outlying and central electrodes, than the two outlying electrodes.

2. The device according to claim 1 in which arranged on the tubular member is a casing including a port for the passage therethrough of electrical conductors for attachment to the electrodes.

3. The device according to claim 2 in which the casing defines an electrically insulating air gap surrounding at least a major portion of the length of the tubular member.

4. The device according to claim 1 in which an active guard is present to shield the electrodes form earth.

5. The device according to claim 4 in which the active guard is in the form of an elongate metal cylinder.

6. A method for monitoring the accumulation of deposits on the interior surface of a pipe or vessel in which a fluid flows comprising:

attaching a device to the pipe or vessel, the device comprising: a tubular member having an internal cross-sectional configuration substantially matching that of the pipe or vessel and formed from an electrically insulating material, and three, spaced ring-like electrodes extending circumferentially around the outside surface of the tubular member and electrically insulated from one another;

applying an electrical potential to the three electrodes and measuring a dielectric constant; monitoring any change of the dielectric constant as indicative of the accumulation of the deposits on the interior surface of a pipe or vessel.

\* \* \* \* \*